US009215868B2

(12) United States Patent
Baur et al.

(10) Patent No.: US 9,215,868 B2
(45) Date of Patent: Dec. 22, 2015

(54) LOW-FOAM PREPARATIONS FOR CROP PROTECTION

(71) Applicant: Bayer Intellectual Property GmbH, Monheim (DE)

(72) Inventors: Peter Baur, Schondorf (DE); Thomas Auler, Leichlingen (DE); Roland Deckwer, Frankfurt (DE); Stephanie Giessler, Frankfurt (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/135,627

(22) Filed: Dec. 20, 2013

(65) Prior Publication Data

US 2014/0121285 A1 May 1, 2014

Related U.S. Application Data

(62) Division of application No. 11/765,039, filed on Jun. 19, 2007, now Pat. No. 8,637,432.

(30) Foreign Application Priority Data

Jun. 21, 2006 (EP) .................................... 06012771

(51) Int. Cl.
| | |
|---|---|
| *A01N 25/02* | (2006.01) |
| *F24C 15/00* | (2006.01) |
| *F24C 15/04* | (2006.01) |
| *A01N 25/04* | (2006.01) |
| *C05G 3/00* | (2006.01) |
| *F24C 15/02* | (2006.01) |

(52) U.S. Cl.
CPC ............... *A01N 25/02* (2013.01); *A01N 25/04* (2013.01); *C05G 3/0005* (2013.01); *F24C 15/006* (2013.01); *F24C 15/023* (2013.01); *F24C 15/04* (2013.01)

(58) Field of Classification Search
CPC ..... A01N 25/02; A01N 25/04; C05G 3/0005; F24C 15/006; F24C 15/023; F24C 15/04
USPC ......... 504/118, 127, 141, 142, 147, 148, 194; 524/457; 71/64.01
See application file for complete search history.

(56) References Cited

U.S. PATENT DOCUMENTS

| | | | |
|---|---|---|---|
| 3,973,944 A * | 8/1976 | Erdmann et al. ............... 504/299 |
| 4,182,621 A | 1/1980 | Ogata et al. | |
| 4,400,196 A | 8/1983 | Albrecht et al. | |
| 4,731,201 A | 3/1988 | Robbins et al. | |
| 5,037,992 A * | 8/1991 | Ward et al. ....................... 558/36 |
| 5,258,358 A | 11/1993 | Kocur et al. | |
| 5,332,714 A | 7/1994 | Albrecht et al. | |
| 5,491,125 A | 2/1996 | Albrecht et al. | |
| 6,770,594 B2 * | 8/2004 | Bickers et al. ................. 504/212 |
| 8,901,041 B2 * | 12/2014 | Frisch et al. ................... 504/362 |
| 2003/0212195 A1 | 11/2003 | Matsumoto et al. | |
| 2005/0266999 A1 | 12/2005 | Frisch et al. | |
| 2006/0183643 A1 | 8/2006 | Cush et al. | |

FOREIGN PATENT DOCUMENTS

| | | | |
|---|---|---|---|
| DE | 2810998 | 9/1978 | |
| DE | 2743607 | 4/1979 | |
| DE | 3726094 | 2/1988 | |
| EP | 0 048 436 | 3/1982 | |
| EP | 0098632 | 1/1984 | |
| EP | 0167337 | 1/1986 | |
| EP | 0 336 151 | 10/1989 | |
| EP | 0 407 874 | 1/1991 | |
| EP | 0436947 | 7/1991 | |
| EP | 0 523 746 | 1/1993 | |
| EP | 1 093 722 | 4/2001 | |
| GB | 2006255 | 5/1979 | |
| GB | 2006255 A * | 5/1979 | ............... C11D 3/60 |
| JP | 54107525 | 8/1979 | |
| JP | 01207125 | 8/1989 | |
| JP | 05323523 | 12/1993 | |
| JP | 06108092 | 4/1994 | |
| JP | 2010/184358 | 8/2010 | |
| WO | WO 9109011 | 6/1991 | |
| WO | WO 9945780 | 9/1999 | |
| WO | WO 00/65005 | 11/2000 | |
| WO | WO 01/09011 | 2/2001 | |
| WO | WO 0207519 | 1/2002 | |
| WO | WO 2005/117583 | 12/2005 | |

OTHER PUBLICATIONS

Database WPI Week 199402, Thomson Scientific, London GB; AN 1994-013476 XP002449830.
Database WPI Week 199420, Thomson Scientific, London GB; AN 1994-164277, XP002449831.
Database CA [online] Chemical Abstracts Service, Columbus, Ohio, US, XP002449826.
Database WPI Week 198939, Thomson Scientific, London GB; AN 1989-282477, XP002449832.
Extended European Search Report (EP 11165151.9-1219/2366287) dated Apr. 4, 2012.

* cited by examiner

*Primary Examiner* — Jane C Oswecki
(74) *Attorney, Agent, or Firm* — Frommer Lawrence & Haug

(57) ABSTRACT

Alkyl ether sulfates having 1 to 9 carbon atoms in the alkyl chain and 1 to 20 alkyleneoxy units in the ether moiety are suitable for use as low-foam additives for enhancing the activity of water-soluble or partially water-soluble agrochemicals. They can be used to produce low-foam preparations for crop protection.

33 Claims, No Drawings ized by a combination of high defoamer activity and
LOW-FOAM PREPARATIONS FOR CROP PROTECTION The present application is a continuation of U.S. patent application Ser. No. 11/765,039 filed on Jun. 19, 2007, which claims priority from German Patent Application No. DE 06012771.9 filed on Jun. 21, 2006, the disclosures of which are incorporated herein by reference in their entirety.

1. FIELD OF THE INVENTION

The invention relates to the technical field of preparations (formulations) for agrochemicals, such as active ingredients in the crop protection field (agrochemically active ingredients, fertilizers), especially formulations of water-soluble or partially water-soluble active crop protectant ingredients (also called "active ingredients in crop protection"), in particular formulations of saltlike active crop protectant ingredients, especially of glufosinate salts such as glufosinate-ammonium salt, according to ISO also referred to as glufosinate-ammonium. The invention also relates to mixtures of adjuvants which can be used in combination with the stated agrochemicals and formulations thereof.

It is noted that citation or identification of any document in this application is not an admission that such document is available as prior art to the present invention.

Aqueous formulations of glufosinate-ammonium are known, for example, from EP-A-0048436, EP-A-00336151 and EP-A-1093722. Here, preference is given to using alkyl ether sulfates having alkyl chains length of C12-C16 with 1 to 10 ethyleneoxy units which are suitable for enhancing the biological action of glufosinate applied to the green parts of plants. The specific mechanism of action of the alkyl ether sulfates in this context is unknown. Compared to the alkyl ether sulfates mentioned, other additives having comparable surfactant properties (spray adherence, spreading on the target plants) including other anionic surfactants reduce the activity. Substances having solvent character, such as polyether glycols, glycerol, mineral oil, mineral oil concentrates, polymers, buffer and other substances do not display any comparable activity either.

Because of the C12-C16-alkyl ether sulfates of the type mentioned that are present in the formulations, the formulations exhibit unfavorable foam behavior when diluted with water prior to application, and during spraying in the course of application, unless defoamers are added.

The consequences then are often overflow of spray apparatus, contamination of the environment, uneven spray deposits on the crops, and crop protectant ingredient residues in the spray apparatus.

For aqueous liquid crop protectant ingredients, EP-A-0407874 proposed effective defoamers from the group of the perfluoroalkylphosphinic or -phosphonic acids. Defoamers of this kind (for example ®Fluowet PP from Clariant) are distinguished by a combination of high defoamer activity and comparatively low application rate, the defoamer activity remaining stable even on prolonged storage at different temperatures and in the event of mechanical stress acting on the formulations. Furthermore, the biological activity of the formulated crop protectant ingredients is unaffected by the defoamer content.

The known fluorinated defoamers, however, are not equally suitable for all fields of application. In the case of many such formulations, for example, the defoaming activity is dependent on the hardness of the water (the calcium and magnesium salt content) used to prepare the spray liquors. From general ecotoxicological considerations as well, it is desirable to reduce the amount of fluorinated hydrocarbons in the environment.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of any previously described product, method of making the product, or process of using the product.

SUMMARY OF THE INVENTION

For the reasons mentioned, there is therefore a need for alternative solutions which allow low-foam formulations of agrochemicals, for example active crop protectant ingredients, such as glufosinate, or fertilizers, to be produced which have good technical properties, for example good storage stability, and uniform and high biological activity.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The invention provides agrochemical preparations, preferably liquid aqueous agrochemical preparations, such as active crop protectant ingredients and/or fertilizers, comprising (a) one or more water-soluble or partially water-soluble agrochemicals, preferably active crop protectant ingredients and/or fertilizers, (active ingredients of type (a)), (b) if desired, one or more water-insoluble or largely water-insoluble agrochemicals, preferably active crop protectant ingredients and/or fertilizers, (active ingredients of type (b)), (c) alkyl ether sulfates having 1 to 9 carbon atoms in the alkyl chain and 1 to 20 alkyleneoxy units in the ether moiety, preferably having a (poly)alkyleneoxy group with 1 to 20 identical or different C1-C4-alkyleneoxy units, which group contains an ethyleneoxy group terminally esterified with the sulfate group, (d) if desired, anionic, nonionic, cationic and/or zwitterionic surfactants, (e) if desired, water and (f) if desired, other customary formulation auxiliaries.

The formulations of the invention, containing defoamer, are suitable preferably for active ingredients of type (a) from the group of the salt-like (salt-containing) water-soluble active ingredients such as glufosinate (salts), glyphosate (salts), paraquat, diquat and the like, especially glufosinate-ammonium. Suitable active ingredients are generally those which, during preparation of aqueous spray liquors, are fully or partially dissolved in the aqueous phase, generally dissolved by 1 to 100 percent by weight, preferably by 5 to 100 percent by weight, more preferably by 10 to 100 percent by weight, in particular by 20 to 100 percent by weight, very particularly preferably by 30 to 100 percent by weight, based on the weight of the active ingredient in the spray liquor, preferably at the active ingredient concentrations customary in practice. Examples of such active ingredients are, in addition to the active crop protectant ingredients mentioned above, those from the group of the herbicides, fungicides, insecticides, acaricides, anthelmintics and other active ingredients, such as plant growth regulators and safeners, preferably active ingredients such as, for example, iodosulfuron-methyl-sodium, imidacloprid, thiacloprid, prothioconazole and triadimenol.

Preference is given here to active ingredients having a solubility in water of more than 10 mg of active ingredient per liter of water, preferably more than 20 mg/l, in particular more than 30 mg/l, at room temperature.

Suitable active ingredients of type a) also include partially water-soluble fertilizers, preferably foliar fertilizers (fertilizers which are taken up by the leaves of the plants), such as urea or foliar macro- or microelement fertilizer, including chelates.

Also suitable is the combination of active crop protectant ingredients, such as herbicides, insecticides and fungicides, and, if desired, fertilizers as active ingredients of type (a).

The formulations of the invention may further also comprise active ingredients of type (b), which are largely insoluble in water, examples being herbicides from the group of the diphenyl ethers such as oxyfluorfen, carbamates, thiocarbamates, triphenyltin compounds and tributyltin compounds, haloacetanilides, phenoxyphenoxyalkanecarboxylic acid derivatives and heteroaryloxyphenoxyalkanecarboxylic acid derivatives, such as quinolyloxy-, quinoxalyloxy-, pyridyloxy-, benzoxalyloxy- and benzothiazolyloxyphenoxyalkanecarboxylic esters, examples being diclofop-methyl, fenoxaprop-ethyl and fenoxaprop-P-ethyl. Here, "largely insoluble in water" is to be understood as meaning that, in aqueous spray liquors, generally less than 1 percent by weight, preferably less than 0.5% by weight, in particular less than 0.1 percent by weight of the active ingredient, based on the weight of the active ingredient in the spray liquor, is dissolved, preferably at the active ingredient concentrations customary in practice.

Here, preference is given to active ingredients having a solubility in water of less than 10 mg of active ingredient per liter of water, preferably less than 2 mg of active ingredient per liter of water.

Also suitable are correspondingly insoluble active ingredients from classes of substances which normally include active ingredients of different solubilities, examples being active ingredients from the group of the cyclohexanedione derivatives, imidazolinones, pyrimidyloxypyridinecarboxylic acid derivatives, pyrimidyloxybenzoic acid derivatives, sulfonylureas, triazolopyrimidinesulfonamide derivatives, and S-(N-aryl-N-alkylcarbamoylmethyl)dithiophosphoric esters.

The stated common names for active ingredients, such as glufosinate, glyphosate, oxyfluorfen, diclofop-methyl, fenoxaprop-(P-)ethyl and others, are known to the skilled worker; see, for example, "The Pesticide Manual" British Crop Protection Council, 13th or 14th Edition, 2003 and 2006, respectively; or "The Compendium of Pesticide Common Names" (available, amongst other things, over the Internet); the names include the known derivatives such as salts of glufosinate and glyphosate, especially the commercially customary forms.

Correspondingly it is also possible for active ingredients from the group of the safeners, growth regulators, insecticides and fungicides to be suitable as component (b) and/or, given good water-solubility, as components (a).

The nature of the active ingredients of type (a) and (b) employed determines the field of use of the agrochemical formulations, preferably crop protectant ingredients or fertilizers. Many crop protectant ingredients, for example, are directed toward the control of harmful organisms. In the case of herbicides, unwanted plants are the type of harmful organisms which can be controlled by using the crop protectant ingredients or agrochemical formulations; in the case of insecticides, the harmful organisms are harmful insects and in the case of fungicides the harmful organisms are harmful fungi. Also suitable here are mixtures of the ingredients and thus combinations of the application fields.

Preference is given to formulations with active ingredients of type (a) from the group comprising one or more compounds of the formula (1) or salts thereof,

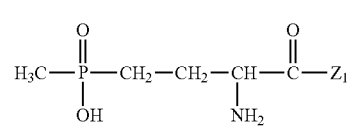

(1)

in which
$Z_1$ is a radical of the formula —OM, —NHCH(CH$_3$)CONHCH(CH$_3$)CO$_2$M or —NHCH(CH$_3$)CONHCH[CH$_2$CH(CH$_3$)$_2$]CO$_2$M, where
M=H or a salt-forming cation,
and/or one or more compounds of the formula (2) or salts thereof,

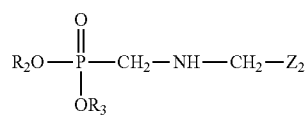

(2)

in which
$Z_2$ is a radical of the formula CN or CO$_2$R$_1$, in which R$_1$=Q or a salt-forming cation and Q=H, alkyl, alkenyl, alkoxyalkyl or C$_6$-C$_{10}$-aryl which is unsubstituted or substituted and is preferably unsubstituted or substituted by one or more radicals from the group consisting of alkyl, alkoxy, halogen, CF$_3$, NO$_2$ and CN, and
R$_2$, R$_3$ each independently of one another are H, alkyl, C$_6$-C$_{10}$-aryl which is unsubstituted or substituted and is preferably unsubstituted or substituted by one or more radicals from the group consisting of alkyl, alkoxy, halogen, CF$_3$, NO$_2$ and CN, or are biphenyl or a salt-forming cation.

Preferably, the carbon-containing radicals associated with Q, $R_2$ or $R_3$ have up to 10 carbon atoms, in particular up to 6 carbon atoms.

The compounds of the formula (1) include an asymmetric carbon atom. The L enantiomer is regarded as the biologically active isomer. The formula (1) hence embraces all stereoisomers and mixtures thereof, particularly the racemate and the biologically active enantiomer in each case. Examples of active ingredients of the formula (1) are as follows:

glufosinate and its ammonium salt in racemic form, i.e., 2-amino-4-[hydroxy(methyl)phosphinoyl]butanoic acid and its salts, such as the ammonium salt or the sodium salt, the L enantiomer of glufosinate and its salts, such as the ammonium salt or the sodium salt, bilanafos/bialaphos, i.e., L-2-amino-4-[hydroxy(methyl) phosphinoyl]-butanoyl-L-alaninyl-L-alanine and its sodium salt.

The racemate of glufosinate-ammonium is on its own delivered usually at doses of between 200 and 1000 g a.i./ha (i.e., grams of active ingredient per hectare). In these doses, glufosinate-ammonium is particularly effective when it is taken up by green parts of the plants; see "The Pesticide Manual" 13th or 14th Edition, British Crop Protection Council 2003 and 2006, respectively. Glufosinate-ammonium is used predominantly for controlling broadleaf and gramineous weeds in plantation crops and on uncultivated land and also, using special application techniques, for inter-row control in arable crops such as corn, cotton, etc. Its use is also of increasing significance in transgenic crops which are tolerant or resistant to the active ingredient, for example in glufosinate-tolerant crops such as ®LibertyLink oilseed rape, ®LibertyLink corn or ®LibertyLink cotton.

The compounds of the formula (2) comprise N-(phosphonoalkyl)glycine and hence derivatives of the amino acid glycine. The herbicidal properties of N-(phosphonomethyl)glycine (glyphosate) are described for example in U.S. Pat. No. 3,799,758.

In crop protection formulations, glyphosate is used generally in the form of the water-soluble salts, the isopropylammonium salt in particular being of importance in connection with the present invention; see "The Pesticide Manual" 13th or 14th Edition, British Crop Protection Council 2003 and 2006, respectively. Similarly to glufosinate-ammonium, glyphosate-isopropylammonium is used for controlling broadleaf and gramineous weeds in plantation crops and on uncultivated land. Its use is also of increasing significance in transgenic crops which are tolerant or resistant to the active ingredient, for example in glyphosate-tolerant crops such as ®Roundup-Ready corn, ®Roundup-Ready soybean, ®Roundup-Ready oilseed rape and ®Roundup-Ready cotton.

The component (c) according to the invention relates to alkyl ether sulfates having 1 to 9 carbon atoms in the alkyl chain and 1 to 20 alkyleneoxy units, preferably 1 to 12 alkyleneoxy units, in the ether moiety, the term alkyl ether sulfates referring to compounds from the group of the (C1-C9)alkyl (poly)glycol ether sulfates, generally having a terminal sulfate group.

The (poly)alkyleneoxy group may contain identical or different alkyleneoxy units, for example C1-C4-alkyleneoxy units such as 1,2-ethyleneoxy [—CH2CH2-O—], also referred to in short as "ethyleneoxy group" or "EO", 1,2-propyleneoxy [—CH(CH3)CH2-O—], 2,3-propyleneoxy [—CH2CH(CH3)-O—], 1,2-butyleneoxy [—CH2CH(C2H5)-O—], 2,3-butyleneoxy [—CH(CH3)CH(CH3)-O—], 3,4-butyleneoxy [—CH(C2H5)CH2-O—], 1,1-dimethyl-1,2-ethyleneoxy [—C(CH3)2CH2-O—] and 2,2-dimethyl-1,2-ethyleneoxy [—CH2C(CH3)2-O—].

Preference is given here to (poly)alkyleneoxy groups containing terminally a 1,2-ethyleneoxy group esterified with the sulfate group, i.e. the last alkyleneoxy unit in the polyalkyleneoxy group, which carries the sulfate group, is preferably an EO unit.

Particularly preferred components (c) are (C1-C9)alkyl (poly)ethylene glycol ether sulfates having 1 to 20 EO, preferably 1 to 10 EO.

In the case of groups having 3 or more carbon atoms, the alkyl radicals in the (C1-C9)alkyl group can be straight-chain or branched.

The alkyl ether sulfates are anionic surfactants. Suitable counterions in these anionic compounds are generally all cations suitable for use in agriculture, for example alkali metal cations such as sodium or potassium, alkaline earth metal cations, such as magnesium or calcium, ammonium or organically substituted ammonium ions such as alkylammonium, dialkylammonium, trialkylammonium, for example trimethylammonium, isopropylammonium. Other cationic groups such as the trimesium ion (known from sulfosate) or alkoxylated ammonium ions are also suitable.

Suitable alkyl ether sulfates are, for example, methyl (poly)glycol ether sulfate, ethyl (poly)glycol ether sulfate, propyl (poly)glycol ether sulfate, such as n-propyl or isopropyl (poly)glycol ether sulfate, butyl (poly)glycol ether sulfate, such as n-butyl, isobutyl, sec-butyl or tert-butyl (poly)glycol ether sulfate, pentyl (poly)glycol ether sulfate, such as n-pentyl or isopentyl (poly)glycol ether sulfate, hexyl (poly)glycol ether sulfate, such as n-hexyl, 1-methylpentyl or isohexyl (poly)glycol ether sulfate, heptyl (poly)glycol ether sulfate, such as n-heptyl or 1-methylhexyl (poly)glycol ether sulfate, octyl (poly)glycol ether sulfate, such as n-octyl, isooctyl or 2-ethylhexyl (poly)glycol ether sulfate, and nonyl (poly)glycol ether sulfate, such as n-nonyl (poly) glycol ether sulfate, each containing (poly)glycol ether moieties of 1 to 20 alkylene glycol units, where the (poly)alkylene glycol groups mentioned as being preferred are preferred. More preferred are the (poly)glycol ether moieties of 1 to 10 ethyleneoxy units (more specifically 1,2-ethyleneoxy units). The counterions are preferably sodium, potassium and ammonium ions. Specific examples of component (c) are listed in Table A1 below.

In the table A1 alkyl (poly)ethylene glycol ether sulfates of the formula (A1) are listed,

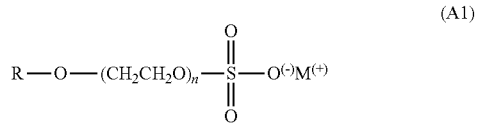

(A1)

In which

R is an alkyl group, n is an integer of 1 to 10 and means the number of ethyleneoxy units in the (poly)ethyleneoxy bridge and M(+) is a cation, preferably H(+) or a metal ion or an ammonium ion, wherein R and n of each compound are specifically indicated in the respective compound name.

TABLE A1

SPECIFIC ETHYLENE GLYCOL ETHER SULFATES methyl ethylene glycol ether sulfate,
methyl diethylene glycol ether sulfate,
methyl triethylene glycol ether sulfate,
methyl tetraethylene glycol ether sulfate,
methyl pentaethylene glycol ether sulfate,
methyl hexaethylene glycol ether sulfate,
methyl heptaethylene glycol ether sulfate,
methyl octaethylene glycol ether sulfate,
methyl nonaethylene glycol ether sulfate,
methyl decaethylene glycol ether sulfate,
ethyl ethylene glycol ether sulfate,
ethyl diethylene glycol ether sulfate,
ethyl triethylene glycol ether sulfate,
ethyl tetraethylene glycol ether sulfate,
ethyl pentaethylene glycol ether sulfate,
ethyl hexaethylene glycol ether sulfate,
ethyl heptaethylene glycol ether sulfate,
ethyl octaethylene glycol ether sulfate,
ethyl nonaethylene glycol ether sulfate,
ethyl decaethylene glycol ether sulfate,
n-propyl ethylene glycol ether sulfate,
n-propyl diethylene glycol ether sulfate,
n-propyl triethylene glycol ether sulfate,
n-propyl tetraethylene glycol ether sulfate,
n-propyl pentaethylene glycol ether sulfate,
n-propyl hexaethylene glycol ether sulfate,
n-propyl heptaethylene glycol ether sulfate,
n-propyl octaethylene glycol ether sulfate,
n-propyl nonaethylene glycol ether sulfate,
n-propyl decaethylene glycol ether sulfate,
isopropyl ethylene glycol ether sulfate,
isopropyl diethylene glycol ether sulfate,
isopropyl triethylene glycol ether sulfate,
isopropyl tetraethylene glycol ether sulfate,
isopropyl pentaethylene glycol ether sulfate,
isopropyl hexaethylene glycol ether sulfate,
isopropyl heptaethylene glycol ether sulfate,
isopropyl octaethylene glycol ether sulfate,
isopropyl nonaethylene glycol ether sulfate,
isopropyl decaethylene glycol ether sulfate,
n-butyl ethylene glycol ether sulfate,
n-butyl diethylene glycol ether sulfate,
n-butyl triethylene glycol ether sulfate,
n-butyl tetraethylene glycol ether sulfate,
n-butyl pentaethylene glycol ether sulfate,
n-butyl hexaethylene glycol ether sulfate,
n-butyl heptaethylene glycol ether sulfate,
n-butyl octaethylene glycol ether sulfate,
n-butyl nonaethylene glycol ether sulfate,
n-butyl decaethylene glycol ether sulfate,
isobutyl ethylene glycol ether sulfate,
isobutyl diethylene glycol ether sulfate,
isobutyl triethylene glycol ether sulfate,
isobutyl tetraethylene glycol ether sulfate,
isobutyl pentaethylene glycol ether sulfate,
isobutyl hexaethylene glycol ether sulfate,
isobutyl heptaethylene glycol ether sulfate,
isobutyl octaethylene glycol ether sulfate,
isobutyl nonaethylene glycol ether sulfate,
isobutyl decaethylene glycol ether sulfate,
sec-butyl ethylene glycol ether sulfate,
sec-butyl diethylene glycol ether sulfate,
sec-butyl triethylene glycol ether sulfate,
sec-butyl tetraethylene glycol ether sulfate,
sec-butyl pentaethylene glycol ether sulfate,
sec-butyl hexaethylene glycol ether sulfate,
sec-butyl heptaethylene glycol ether sulfate,
sec-butyl octaethylene glycol ether sulfate,
sec-butyl nonaethylene glycol ether sulfate,
sec-butyl decaethylene glycol ether sulfate,
tert-butyl ethylene glycol ether sulfate,
tert-butyl diethylene glycol ether sulfate,
tert-butyl triethylene glycol ether sulfate,
tert-butyl tetraethylene glycol ether sulfate,
tert-butyl pentaethylene glycol ether sulfate,
tert-butyl hexaethylene glycol ether sulfate,
tert-butyl heptaethylene glycol ether sulfate,
tert-butyl octaethylene glycol ether sulfate,
tert-butyl nonaethylene glycol ether sulfate,
tert-butyl decaethylene glycol ether sulfate,
n-pentyl ethylene glycol ether sulfate,
n-pentyl diethylene glycol ether sulfate,
n-pentyl triethylene glycol ether sulfate,
n-pentyl tetraethylene glycol ether sulfate,
n-pentyl pentaethylene glycol ether sulfate,
n-pentyl hexaethylene glycol ether sulfate,
n-pentyl heptaethylene glycol ether sulfate,
n-pentyl octaethylene glycol ether sulfate,
n-pentyl nonaethylene glycol ether sulfate,
n-pentyl decaethylene glycol ether sulfate,
isopentyl ethylene glycol ether sulfate,
isopentyl diethylene glycol ether sulfate,
isopentyl triethylene glycol ether sulfate,
isopentyl tetraethylene glycol ether sulfate,
isopentyl pentaethylene glycol ether sulfate,
isopentyl hexaethylene glycol ether sulfate,
isopentyl heptaethylene glycol ether sulfate,
isopentyl octaethylene glycol ether sulfate,
isopentyl nonaethylene glycol ether sulfate,
isopentyl decaethylene glycol ether sulfate,
n-hexyl ethylene glycol ether sulfate,
n-hexyl diethylene glycol ether sulfate,
n-hexyl triethylene glycol ether sulfate,
n-hexyl tetraethylene glycol ether sulfate,
n-hexyl pentaethylene glycol ether sulfate,
n-hexyl hexaethylene glycol ether sulfate,
n-hexyl heptaethylene glycol ether sulfate,
n-hexyl octaethylene glycol ether sulfate,
n-hexyl nonaethylene glycol ether sulfate,
n-hexyl decaethylene glycol ether sulfate,
n-heptyl ethylene glycol ether sulfate,
n-heptyl diethylene glycol ether sulfate,
n-heptyl triethylene glycol ether sulfate,
n-heptyl tetraethylene glycol ether sulfate,
n-heptyl pentaethylene glycol ether sulfate,
n-heptyl hexaethylene glycol ether sulfate,
n-heptyl heptaethylene glycol ether sulfate,
n-heptyl octaethylene glycol ether sulfate,
n-heptyl nonaethylene glycol ether sulfate,
n-heptyl decaethylene glycol ether sulfate,
n-octyl ethylene glycol ether sulfate,
n-octyl diethylene glycol ether sulfate,
n-octyl triethylene glycol ether sulfate,
n-octyl tetraethylene glycol ether sulfate,
n-octyl pentaethylene glycol ether sulfate,
n-octyl hexaethylene glycol ether sulfate,
n-octyl heptaethylene glycol ether sulfate,
n-octyl octaethylene glycol ether sulfate,
n-octyl nonaethylene glycol ether sulfate,
n-octyl decaethylene glycol ether sulfate,
2-ethylhexyl ethylene glycol ether sulfate,
2-ethylhexyl diethylene glycol ether sulfate,
2-ethylhexyl triethylene glycol ether sulfate,
2-ethylhexyl tetraethylene glycol ether sulfate,
2-ethylhexyl pentaethylene glycol ether sulfate,
2-ethylhexyl hexaethylene glycol ether sulfate,
2-ethylhexyl heptaethylene glycol ether sulfate,
2-ethylhexyl octaethylene glycol ether sulfate,
2-ethylhexyl nonaethylene glycol ether sulfate,
2-ethylhexyl decaethylene glycol ether sulfate,
n-nonyl ethylene glycol ether sulfate,
n-nonyl diethylene glycol ether sulfate,
n-nonyl triethylene glycol ether sulfate,
n-nonyl tetraethylene glycol ether sulfate,
n-nonyl pentaethylene glycol ether sulfate,
n-nonyl hexaethylene glycol ether sulfate,
n-nonyl heptaethylene glycol ether sulfate,
n-nonyl octaethylene glycol ether sulfate,
n-nonyl nonaethylene glycol ether sulfate,
n-nonyl decaethylene glycol ether sulfate, wherein in each case any salts and mixtures thereof are preferred, more preferably alkali metal salts having $M^{(+)}$ = an alkali metal cation as counter ion or ammonium salts having preferably $M^{(+)} = NH_4^+$ as counter ion and wherein their sodium salts, potassium salts or ammonium salts, in particular their sodium salts, being especially preferred.

The special salts then make up a list of individual compounds corresponding to Table A1, where, for reference purposes, the sodium salts make up a Table A2 which corresponds to Table A1 (not repeated individually), the potassium salts make up a Table A3 which corresponds to Table A1 and the ammonium salts make up a Table A4 which corresponds to Table A1, where instead of the ether sulfates the ether sulfate sodium salt or ether sulfate potassium salt or the ether sulfate ammonium salt is listed.

Particular preference is also given to mixtures of sodium and potassium and/or ammonium salts of the ether sulfates of the abovementioned Tables A2, A3 and A4.

From among the additives (c) mentioned, preference is given to compounds having 4 to 8 carbon atoms, in particular 6 to 8 carbon atoms, in the alkyl radical and 1 to 10 ethyleneoxy units. Preference is also given to additives having straight-chain alkyl radicals.

The compounds are novel and/or can be prepared analogously to processes known for alkyl ether sulfates having relatively long alkyl chains. Accordingly, the invention also provides the novel compounds of component (c).

As component (d), the preparation may, if desired, comprise anionic, nonionic, cationic and/or zwitterionic surfactants. These compounds may help to increase or adjust the surface activity to a desired level, in particular if the alkyl ether sulfates employed contain very short alkyl radicals.

Suitable surfactants for component (d) are, for example, the following (where in each case EO=ethylene oxide units, PO=propylene oxide units and BO=butylene oxide units as regards the preparation or respective alkylenoxy units in the tenside molecules):

d1) anionic surfactants such as, for example:
d1-1) anionic derivatives of fatty alcohols having 10-24 carbon atoms with 0-60 EO and/or 0-20 PO and/or 0-15 BO in any order, in the form of ether carboxylates, sulfonates, sulfates and phosphates and their inorganic (for example alkali metal and alkaline earth metal) and organic salts (for example those based on amine or alkanolamine), such as Genapol®LRO, Sandopan® grades, Hostaphat/Hordaphos® grades from Clariant;
d1-2) anionic derivatives of copolymers composed of EO, PO and/or BO units with a molecular weight of 400 to $10^8$, n the form of ether carboxylates, sulfonates, sulfates and phosphates and their inorganic (for example alkali metal and alkaline earth metal) and organic salts (for example those based on amine or alkanolamine);
d1-3) anionic derivatives of alkylene oxide adducts of $C_1$-$C_9$ alcohols, in the form of ether carboxylates, sulfonates, sulfates and phosphates and their inorganic (for example alkali metal and alkaline earth metal) and organic salts (for example those based on amine or alkanolamine), unless their structures are included in the definition of the alkyl ether sulfates of component (c);
d1-4) anionic derivatives of fatty acid alkoxylates in the form of ether carboxylates, sulfonates, sulfates and phosphates and their inorganic (for example alkali metal and alkaline earth metal) and organic salts (for example those based on amine or alkanolamine).

Preferred anionic surfactants are
alkyl polyglycol ether sulfates, especially fatty alcohol diethylene glycol ether sulfate (for example Genapol LRO®, Clariant),
or alkyl polyglycol ether carboxylates (for example 2-(isotridecyloxypolyethylene-oxy)ethyl carboxymethyl ether, Marlowet 4538®, Hüls),
where the amount and the type of additional anionic surfactants is expediently chosen such that no unacceptable foaming of the formulation results.

d2) Cationic or zwitterionic surfactants such as, for example:
d2-1) alkylene oxide adducts of fatty amines, quarternary ammonium compounds having 8 to 22 carbon atoms (C8-C22), such as, for example, Genamin® C, L, O and T grades from Clariant;
d2-2) surface-active, zwitterionic compounds such as taurides, betaines and sulfobetaines in the form of Tegotain® grades from Goldschmidt, Hostapon® and Arkopon®T grades from Clariant.
d3) Nonionic surfactants such as, for example:
d3-1) fatty alcohols having 8-24 carbon atoms with 0-60 EO and/or 0-20 PO and/or 0-15 BO in any order. Examples of such compounds are Genapol® C, L, O, T, UD, UDD and X grades from Clariant, Plurafac® and Lutensol® A, AT, ON and TO grades from BASF, Marlipal®24 and O13 grades from Condea, Dehypon® grades from Henkel, and Ethylan® grades from Akzo-Nobel such as Ethylan CD 120;
d3-2) fatty acid alkoxylates and triglyceride alkoxylates such as the Serdox®NOG grades from Condea or the Emulsogen® grades from Clariant;
d3-3) fatty acid amide alkoxylates such as the Comperlan® grades from Henkel or the Amam® grades from Rhodia;
d3-4) alkylene oxide adducts of alkynediols such as the Surfynol® grades from Air Products; sugar derivatives such as amino sugars and amido sugars from Clariant;
d3-5) glucitols from Clariant;
d3-6) silicone- and/or silane-based surface-active compounds such as the Tegopren® grades from Goldschmidt and the SE® grades from Wacker, and also the Bevaloid®, Rhodorsil®, and Silcolapse® grades from Rhodia (Dow Corning, Reliance, GE, Bayer),
d3-7) surface-active sulfonamides, from Bayer, for example;
d3-8) surface-active polyacrylic and polymethacrylic derivatives such as the Sokalan® grades from BASF;
d3-9) surface-active polyamides such as modified gelatins or derivatized polyaspartic acid from Bayer, and derivatives thereof,
d3-10) surfactant polyvinyl compounds such as modified PVP, such as the Luviskol® grades from BASF and the Agrimer® grades from ISP, or the derivatized polyvinyl acetates, such as the Mowilith® grades from Clariant, or the polyvinyl butyrates, such as the Lutonal® grades from BASF, the Vinnapas® and the Pioloform® grades from Wacker, or modified polyvinyl alcohols, such as the Mowiol® grades from Clariant,
d3-11) surface-active polymers based on maleic anhydride and/or reaction products of maleic anhydride and also maleic anhydride copolymers and/or copolymers containing reaction products of maleic anhydride, such as the Agrimer® VEMA grades from ISP,
d3-12) surface-active derivatives of montan waxes, polyethylene waxes and polypropylene waxes, such as the Hoechst® waxes or the Licowet® grades from Clariant,
d3-13) polyol-based alkylene oxide adducts, such as Polyglycol® grades from Clariant;
d3-14) surface-active polyglycerides and derivatives thereof from Clariant.
d3-15) alkylpolysaccharides and mixtures thereof such as those, for example, from the ®Atplus range from Uniqema, preferably Atplus 435,
d3-16) alkylpolyglycosides in the form of the APG® grades from Henkel, an example being ®Plantaren APG 225 (fatty alcohol $C_8$-$C_{10}$ glucoside), d3-17) sorbitan esters in the form of the Span® or Tween® grades from Uniqema, d3-18) cyclodextrin esters or ethers from Wacker, d3-19) surface-active cellulose derivatives and algin, pectin, and guar derivatives such as the Tylose® grades from Clariant, the Manutex® grades from Kelco, and guar derivatives from Cesalpina, d3-20) alkylpolyglycoside-alkylpolysaccharide mixtures based on $C_8$-$C_{10}$ fatty alcohol, such as ®Glucopon 225 DK and ®Glucopon 215 CSUP (Cognis).

As component (e), the preparation according to the invention may, if desired, comprise water. Preference is given to aqueous, liquid, concentrated, storage-stable formulations. Ready-to-use, aqueous spray liquors are also to be considered as formulations according to the invention.

Likewise according to the invention are water-free or low-water formulations such as dusts or granules or emulsifiable concentrates which are diluted with water to form spray liquors only for application.

As component (f), the preparation according to the invention may, if desired, comprise other customary formulation auxiliaries, such as solvents, inert materials, such as tackifiers, wetting agents, dispersants, emulsifiers, penetrants, preservatives and antifreeze agents, fillers, carriers and colorants, evaporation inhibitors and pH-(buffer, acids and bases) or viscosity-modifying agents (for example thickeners) and, if desired, also antifoams, the latter being suitable only in a reduced amount, if at all.

Customary formulation auxiliaries (f) are, for example, the inert materials, antifreeze agents, evaporation inhibitors, preservatives, colorants, etc., mentioned; preferred formulation auxiliaries (f) are antifreeze agents and evaporation inhibitors, such as glycerol or ethylene glycol, for example in an amount of from 2 to 10% by weight, and preservatives, for example Mergal K9N® (Riedel) or Cobate C®.

Possible components (f) are, for example, organic solvents or inorganic solvents or mixtures thereof. In general, they comprise, in the case of liquid preparations, water (component (e)) as solvent. However, for special applications, dusts or granules are also possible. Even water-free preparations based on organic solvents such as unpolar or polar organic solvents are possible.

Examples of comparatively unpolar solvents in the sense of the invention are aliphatic or aromatic hydrocarbons, such as, for example, mineral oils or toluene, xylenes and naphthalene derivatives, halogenated aliphatic or aromatic hydrocarbons such as methylene chloride or chlorobenzene, oils, for example vegetable oils, such as corn germ oil and rapeseed oil, or oil derivatives, such as rapeseed oil methyl ester.

In the context of the present invention, the term "polar organic solvents" refers, for example, to polar protic or aprotic polar solvents and mixtures thereof.

Examples of polar solvents in the sense of the invention are aliphatic alcohols, such as, for example, lower alkanols, such as methanol, ethanol, propanol, isopropanol and butanol, or polyhydric alcohols, such as ethylene glycol, glycerol, polar ethers, such as tetrahydrofuran (THF), dioxane, alkylene glycol monoalkyl ethers and alkylene glycol dialkyl ethers, such as, for example, propylene glycol monomethyl ether, propylene glycol monoethyl ether, ethylene glycol monomethyl ether or ethylene glycol monoethyl ether, diglyme and tetraglyme;

amides, such as dimethylformamide (DMF), dimethylacetamide, dimethylcaprylamide, dimethylcaprinamide (®Hallcomide) and N-alkylpyrrolidones;

ketones, such as acetone;

esters based on glycerol and carboxylic acids, such as glycerol mono-, di-, and triacetate;

lactames;

lactate esters having chain lengths of 1 to 10 carbon atoms in the ester moiety;

carbonic diesters;

nitriles, such as acetonitrile, propionitrile, butyronitrile, and benzonitrile;

sulfoxides and sulfones, such as dimethyl sulfoxide (DMSO) and sulfolane.

Frequently also suitable are combinations of different solvents additionally comprising alcohols, such as methanol, ethanol, n- and isopropanol, n-, iso-, t- and 2-butanol.

Suitable for monophasic aqueous-organic solutions are fully or largely water-miscible solvents or solvent mixtures.

In the case of single-phase, aqueous-organic solutions, solvents or solvent mixtures which are completely or largely water-miscible are suitable.

Preferred organic solvents in the sense of the present invention are polar organic solvents, such as N-methylpyrrolidone and Dowanol® PM (propylene glycol monomethyl ether).

The auxiliaries needed to prepare the above formulations, such as surfactants in particular, are known in principle and are described for example in: McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" ["Surface-Active Ethyleneoxide Adducts"], Wiss. Verlagsgesellschaft, Stuttgart 1976; Winnacker-Kuchler, "Chemische Technologie" ["Chemical Technology"], Volume 7, C. Hanser-Verlag, Munich, 4th Edition 1986, and references cited in each of these.

The invention also provides the use of the alkyl ether sulfates, if desired in combination with other surfactants, as low-foam additive for enhancing the activity of agrochemicals, preferably active crop protectant ingredients and/or fertilizers, which are water-soluble or partially water-soluble, preferably the active ingredients (a) mentioned. This includes the use according to the invention in spray liquors or in preparations intended for preparing sray liquors, the active ingredients in the spray liquors preferably being fully or partially water-soluble, i.e. generally in an amount of 1 to 100 percent by weight, preferably in an amount of 5 to 100 percent by weight, more preferably in an amount of 10 to 100 percent by weight, in particular in an amount of 20 to 100 percent by weight, very particularly preferably in an amount of 30 to 100 percent by weight, based on the weight of the active ingredient in the spray liquor, and preferably at active ingredient concentrations customary in practice. Preference is given here to the abovementioned active ingredients (a) and the active ingredients mentioned as being preferred in this context.

Here, the compounds can be prepared both in single-compound formulations and in coformulations of active ingredients or be used as an additive in the tank mix process.

By virtue of their surfactant properties, the alkyl ether sulfates (c) promote the uptake of the active ingredients of type a) and type b) into the plant, in particular the uptake via the leaves of the plant, and thus contribute to improving the activity of the active ingredients. Surprisingly, the surfactant properties of the alkyl ether sulfates c) used according to the invention lead to favorable activity improvements in combination with a considerably reduced tendency of the preparations or spray liquors to foam.

The amount of alkyl ether sulfate in the preparations is expediently chosen such that a spray liquor that does not foam or foams comparatively little results when the spray liquors are prepared. The amount depends generally on the chosen chain length in the alkyl moiety and the number of alkyleneoxy units or EO units in the ether sulfate moiety.

The weight ratio of active ingredient (a) (based on 100% of active ingredient) to alkyl ether sulfate (c) (based on detergent substance) can be varied within wide ranges and is preferably in the range of from 1:0.1 to 1:10, in particular from 1:0.5 to 1:5.

With the aid of the component mixtures, it is possible to prepare concentrated low-foam preparations, preferably concentrated low-foam liquid aqueous preparations, of agrochemicals, preferably salt-like active crop protectant ingredients, such as glufosinate-ammonium, which comprise
- (a) from 1 to 40% by weight, preferably from 2 to 30% by weight, in particular from 5 to 20% by weight, of water-soluble or partially water-soluble agrochemicals, preferably active crop protectant ingredients or fertilizers, (active ingredients of type (a)),
- (b) from 0 to 40% by weight, preferably from 0 to 20% by weight, in particular from 0 to 10% by weight, of water-insoluble or largely water-insoluble agrochemicals, preferably active crop protectant ingredients or fertilizers, (active ingredients of type (b)),
- (c) from 0.1 to 99% by weight, preferably from 1 to 80% by weight, in particular from 2 to 70% by weight, very particularly preferably from 5 to 60% by weight, of alkyl ether sulfates having 1 to 9 carbon atoms in the alkyl chain and 1 to 20 alkyleneoxy units,
- (d) from 0 to 25% by weight, preferably from 0 to 20% by weight, in particular from 1 to 20% by weight, very particularly preferably from 3 to 15% by weight, of anionic, nonionic, cationic and/or zwitterionic surfactants,
- (e) from 0 to 95% by weight, preferably from 0.1 to 90% by weight, more preferably from 5 to 85% by weight, of water, in particular from 10 to 60% by weight of water and
- (f) from 0 to 50% by weight, preferably from 0 to 20% by weight, preferably from 0 to 15% by weight, of other customary formulation auxiliaries.

Here, "% by weight" means in each case "percent by weight", i.e. the ratio of the weight of the component and the weight of the preparation in percent.

Preference is also given to formulations in which the amount of the components consists of a combination of two or more of the parts of the components mentioned as being preferred.

The liquid formulations of the invention can be prepared by methods which are customary in principle, i.e., by mixing the components with stirring or shaking or by means of static mixing methods. The liquid formulations obtained are stable with good storage properties.

The invention further provides low-foam liquid adjuvant formulations which can be used for preparing the stated concentrated agrochemical formulations, preferably crop protectant ingredient formulations or fertilizers, or for preparing tank mixes with agrochemicals, preferably active crop protectant ingredient formulations or fertilizers, or else may be applied separately, simultaneously or sequentially with the application of active ingredients (preferably the stated active ingredients (a)) to the plants or to the soil on or in which the plants are growing.

Adjuvant formulations of this kind comprise
- (c) alkyl ether sulfates having 1 to 9 carbon atoms in the alkyl chain and 1 to 20 alkyleneoxy units in the ether moiety,
- (d) if desired, nonionic, cationic and/or zwitterionic surfactants,
- (e) water and
- (f) if desired, other customary formulation auxiliaries, components (c), (d), (e), (f) being as defined for the aforementioned crop protectant ingredient formulations comprising active ingredient.

Preferred liquid adjuvant formulations comprise
- (c) from 0.1 to 99.9% by weight, more preferably from 0.1 to 99% by weight, preferably from 1 to 80% by weight, in particular from 2 to 70% by weight, very particularly preferably from 5 to 60% by weight, of alkyl ether sulfates having 1 to 9 carbon atoms in the alkyl chain and 1 to 20 alkyleneoxy units,
- (d) from 0 to 50% by weight, preferably from 0 to 30% by weight, in particular from 1 to 25% by weight, very particularly preferably from 5-20% by weight, of anionic, nonionic, cationic and/or zwitterionic surfactants,
- (e) from 0.1 to 99.9% by weight, more preferably from 0.1 to 95% by weight, preferably from 5 to 90%, of water, preferably from 10 to 75% of water,
- (f1) from 0 to 60% by weight, preferably from 0 to 40% by weight, in particular from 0 to 30% by weight, of polar organic solvents and
- (f) from 0 to 20% by weight, preferably from 0 to 15% by weight, of other customary formulation auxiliaries.

The liquid formulations comprising active ingredient and the adjuvant formulations are low-foam formulations with good storage properties. In many cases they have very favorable technical properties on application. By way of example the formulations are distinguished by a low tendency to foam when diluted with water, as for example when preparing tank mixes or when the formulations are applied by spraying. The formulations with active ingredient and the adjuvant formulations, when employed together with active ingredients/active ingredient formulations, also display a very good biological action by comparison with known formulations comprising long-chain alkyl ether sulfates.

Accordingly the formulations of the invention are especially suitable for use in crop protection where the formulations are applied, if appropriate after dilution with water, to the plants, to parts of plants or to the area under cultivation.

In the case of herbicidal active ingredients (a) and/or (b) the formulations are very suitable for controlling unwanted plant growth both on uncultivated land and in tolerant crops.

When the active ingredients of type a) used are selective herbicides or insecticides, fungicides or fertilizers, the preparations according to the invention can be employed on their own or in combination as low-foam and effective formulations in the monocotyledonous and dicotyledonous crops customary for the active ingredients, for example in economically important crops, such as cereals (wheat, barley, triticale, rye, rice, corn, millet), sugar beets, sugar cane, oilseed rape, cotton, sunflowers, peas, beans and soybeans. Of particular interest in this context is the application in monocotyledonous crops, such as cereals (wheat, barley, rye, triticale, sorghum), including corn and rice, and monocotyledonous vegetable crops, but also in dicotyledonous crops, such as, for example, soybeans, oilseed rape, cotton, grapevines, vegetables, fruit and ornamental plants. The preparations according to the invention can be employed in the treatment of turf grasses which include but are not limited to rye grass, *Poa* grass and Bermuda grass.

In the case of the preferred active ingredients a), the preparations can be employed alone or in combination with other active ingredients a) and/or fertilizers on uncultivated land, patches of useful plants and ornamental plants or in suitable tolerant crops. Here, in addition to the crops of tolerant useful plants mentioned, such as ®LibertyLink or ®Roundup-Ready crops, for producing field crops, crops for ornamental areas and useful areas, such as turf, are also of interest. For example, the formulations according to the invention comprising glufosinate(-ammonium) with or without fertilizers are suitable for controlling harmful plants on ornamental turf and useful turf, especially ryegrass, meadow-grass or Bermuda grass, preferably specifically in glufosinate-tolerant turf.

The invention is further described by the following non-limiting examples which further illustrate the invention, and are not intended, nor should they be interpreted to, limit the scope of the invention.

In the examples below, the stated amounts are based on weight (b.w.=by weight), unless indicated otherwise. The examples of Tables 1 and 2 relate to stable compositions according to the invention.

TABLE 1

FORMULATIONS (ACCORDING TO THE INVENTION)

| Example No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| active ingredient[1] [% b.w.] | 15 | 25 | 15 | 25 | 15 | 25 | 25 | 25 | 25 | 25 | 25 | 25 | 25 | 25 |
| AES (type[2]) | C9 | C9 | C8 | C8 | C7 | C7 | C6 | C6 | C5 | C5 | C4 | C3 | C2 | C1 |
| AES [% b.w.] | 40 | 30 | 40 | 30 | 40 | 30 | 30 | 40 | 30 | 40 | 40 | 40 | 40 | 40 |
| wetting agent[3] [% b.w.] | 0 | 0 | 0 | 0 | 0 | 0 | 5 | 0 | 5 | 5 | 5 | 5 | 5 | 5 |
| org. solvent[4] | 10 | 15 | 10 | 15 | 10 | 15 | 10 | 10 | 10 | 10 | 10 | 10 | 10 | 10 |
| water [% b.w.] | 35 | 30 | 35 | 30 | 35 | 30 | 30 | 25 | 30 | 20 | 20 | 20 | 20 | 20 |

Abbreviations in Table 1

[1] "active ingredient" refers to the active ingredient glufosinate-ammonium;

[2] "AES" means an alkyl ether sulfate, where "C9" refers to the alkyl chain, i.e. "AES type C9" refers to a nonyl polyethylene glycol ether sulfate mixture having 1 to 10 EO; correspondingly, "C8", "C7", "C6", "C5", "C4", "C3", "C2", "C1" refer to the corresponding octyl, heptyl, hexyl, pentyl, butyl, propyl, ethyl and methyl polyglycol ether sulfate, respectively;

[3] "wetting agent" refers to the nonionic wetting agent tridecylalcohol ethoxylate having 15 EO; comparable formulations are obtained when the nonionic wetting agent mentioned is replaced by other nonionic wetting agents such as alcohol alkoxylates or alkyl glycosides; alternative formulations are obtained when the wetting agents used are ionic wetting agents such a anionic dialkyl sulfosuccinate or cationic wetting agents such as alkyl aminoalkoxylates;

[4] "org. solvent" refers to the organic solvent Dowanol ® PM (propylene glycol monomethyl ether)

TABLE 2

| Example No. | 15 | 16 | 17 | 18 | 19 | 20 | 21 | 22 | 23 | 24 | 25 | 26 |
|---|---|---|---|---|---|---|---|---|---|---|---|---|
| active ingredient[1] [% b.w.] | 5 | 5 | 10 | 10 | 33 | 1 | 1 | 10 | 10 | 1 | 5 | 10 |
| AES (type[2]) | C9 | C9 | C9 | C9 | C9 | C6 | C6 | C6 | C6 | C4 | C4 | C4 |
| AES [% b.w.] | 25 | 2.5 | 2 | 50 | 27 | 8 | 0.5 | 5 | 50 | 4 | 40 | 40 |
| wetting agent[3] [% b.w.] | 3 | 3 | 0 | 0 | 0 | 0 | 3 | 0 | 0 | 2 | 3 | 5 |
| org. solvent[4] | 5 | 5 | 10 | 10 | 0 | 0 | 0 | 10 | 10 | 5 | 5 | 10 |
| water [% b.w.] | 62 | 84.5 | 78 | 40 | 30 | 91 | 95.5 | 75 | 30 | 88 | 50 | 35 |

Abbreviations in Table 2: see abbreviations for Table 1

Foam Test

With stirring, the concentrated liquid crop protectant formulation in question from Tables 1 and 2 was diluted to a 1% strength solution, and the volume of foam formed was determined after 1 min, 3 min and 12 min in ml of volume (see foam assessment according to CIPAC MT 47.2). Alternatively, the additives in question were dissolved on their own at 2 g/l, and the volume of foam formed was determined after 1 min, 3 min and 12 min in ml of volume.

In comparison to formulations in which the alkyl ether sulfates have been replaced by $C_{12}/C_{14}$-fatty alcohol diethylene glycol ether sulfate, formulations comprising alkyl ether sulfates from Table 1 and Table 2 had considerably lower formation of foam. Foam formution was virtually prevented, i.e. for the formulations from Tables 1 and 2 during mixing of an amount of from 0.2 to 5 g/l alkyl ether sulfate in water the volume of foam after 3 min was in each case less than 15 ml, and the volume of foam after 12 min was 0 ml, whereas the amount of from 0.2 to 5 g/l of a corresponding formulation comprising $C_{12}/C_{14}$-fatty alcohol diethylene glycol ether sulfate as AES had a maximum foam volume of 100 ml both after 3 min and after 10 min.

In the test, the $C_{12}/C_{14}$-fatty alcohol diethylene glycol ether sulfate alone at 2 g/l gave a maximum foam volume of 100 ml even after 12 min, whereas in the case of the alkyl ether sulfates from Tables 1 and 2 the measured foam volume after 12 min was in each case 0 ml and even after 3 min less than 10 ml.

In this foam test, after 3 min, the foam volume of formulations comprising $C_{12}/C_{14}$-fatty alcohol diethylene glycol ether sulfate and silicone-based antifoams (for example Rhodorsil® grades) was still 100 ml. In contrast, formulations comprising the alkyl ether sulfates according to the invention showed virtually no more foam after only 3 min even if no additional antifoams were added.

BIOLOGICAL EXAMPLES

1) Application with Glufosinate for Controlling Weeds

The formulations of Table 1 were diluted with water and applied at a water application rate of 200 l/ha to uncultivated land containing a spectrum of harmful plants that had emerged under natural conditions. Evaluation after 4 weeks indicated that the green parts of the harmful plants had died off and hence that effective harmful plant control had been achieved.

2) Application with glufosinate for controlling weeds

The formulations of Tables 1 and 2 were diluted with water so that a water application rate of 200-400 l/ha at a customary application rate for glufosinate (300-1000 g/ha) for application to uncultivated land containing a spectrum of mono- and dicotyledonous harmful plants that had emerged under natural conditions was obtained. Evaluation of the effect after 5 weeks indicated that the green parts of the harmful plants had died off and hence that effective harmful plant control had been achieved. For example, in comparison to formulations comprising $C_{12}/C_{14}$-fatty alcohol diethylene glycol ether sulfate as AES, formulations from columns 1 to 8 of Table 1 and columns 1 to 9 showed, at the same ratio of glufosinate to AES, compatibly good results in biological action with respect to the control of mono- and dicotyledonous harmful plants.

3) Leaf Penetration of Water-Soluble Leaf Fertilisers Such as Urea

In the case of foliar application of urea (0.1 to 2% in the spray liqour) to leaves of monocotyledonous crop plants such as corn and also to dicotyledonous crop plants such as apples, the rate of foliar uptake was increased within a number of days by a factor of at least two in the presence of 0.05 to 1% of one of the alkyl ether sulfates according to the invention.

4) Uptake of Insecticides

In the case of foliar application of chloronicotinyl insecticides such as imidacloprid, at imidacloprid:alkyl ether sulfate ratios of from 4:1 to 1:4, the uptake of the active ingredient achieved for penetration of apple leaves, for example, was 2 to 5 times faster than in the case of imidacloprid formulations not comprising any alkyl ether sulfate (such as, for example, ®Confidor SL200 or SC350).

Having thus described in detail various embodiments of the present invention, it is to be understood that the invention defined by the above paragraphs is not to be limited to particular details set forth in the above description as many apparent variations thereof are possible without departing from the spirit or scope of the present invention.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. An adjuvant formulation comprising:
(c) one or more 2-ethylhexyl (poly)glycol ether sulfates having 1 to 20 alkyleneoxy units in the ether moiety, each 2-ethylhexyl (poly)glycol ether sulfate having the formula:

$$R\text{---}O\text{---}(R^1O)_n\text{---}SO_3:$$

where:
R is 2-ethylhexyl;
$R^1$ is alkylene; and
n is 1 to 20;
(d) optionally, one or more surfactants selected from the group consisting of nonionic, cationic, and zwitterionic surfactants;
(e) water;
(f1) optionally, one or more polar organic solvents; and
(f) optionally, one or more other customary formulation auxiliaries;
wherein component (e) is present in an amount of from 0.1 to 95% by weight.

2. The adjuvant formulation according to claim 1;
wherein the component (c) 2-ethylhexyl (poly)glycol ether sulfate has 1 to 10 ethyleneoxy units in the ether moiety.

3. The adjuvant formulation according to claim 2;
wherein the component (c) 2-ethylhexyl (poly)glycol ether sulfate has 1,2-ethyleneoxy units in the ether moiety.

4. The adjuvant formulation according to claim 1;
wherein a counterion of the 2-ethylhexyl (poly)glycol ether sulfate is a sodium, potassium, or ammonium ion.

5. The adjuvant formulation according to claim 4;
wherein the counterion is a sodium.

6. The adjuvant formulation according to claim 1;
wherein component (c) is present in an amount of from 0.1 to 99.9% by weight;
wherein component (d) is present in an amount of from 0 to 50% by weight;
wherein component (e) is present in an amount of from 0.1 to 95% by weight;
wherein component (f1) is present in an amount of from 60% by weight; and wherein component (f) is present in an amount of from 0 to 20% by weight.

7. The adjuvant formulation according to claim 6;
wherein component (c) is present in an amount of from 0.1 to 99% by weight.

8. The adjuvant formulation according to claim 7;
wherein component (c) is present in an amount of from 1 to 80% by weight.

9. The adjuvant formulation according to claim 8;
wherein component (c) is present in an amount of from 2 to 70% by weight.

10. The adjuvant formulation according to claim 9;
wherein component (c) is present in an amount of from 5 to 60% by weight.

11. The adjuvant formulation according to claim 6;
wherein component (d) is present in an amount of from 0 to 30% by weight.

12. The adjuvant formulation according to claim 11;
wherein component (d) is present in an amount of from 1 to 25% by weight.

13. The adjuvant formulation according to claim 12;
wherein component (d) is present in an amount of from 5-20% by weight.

14. The adjuvant formulation according to claim 6;
wherein component (e) is present in an amount of from 0.1 to 95% by weight.

15. The adjuvant formulation according to claim 14;
wherein component (e) is present in an amount of from 5 to 90% by weight.

16. The adjuvant formulation according to claim 15;
wherein component (e) is present in an amount of from 10 to 75% by weight.

17. The adjuvant formulation according to claim 6;
wherein component (f1) is present in an amount of from 0 to 40% by weight.

18. The adjuvant formulation according to claim 17;
wherein component (f1) is present in an amount of from 0 to 30% by weight.

19. The adjuvant formulation according to claim 6;
wherein component (f) is present in an amount of from 0 to 15% by weight.

20. The adjuvant formulation according to claim 1;
wherein the 2-ethylhexyl (poly)glycol ether sulfate is selected from the group consisting of:
2-ethylhexyl ethylene glycol ether sulfate;
2-ethylhexyl diethylene glycol ether sulfate;
2-ethylhexyl triethylene glycol ether sulfate;
2-ethylhexyl tetraethylene glycol ether sulfate;
2-ethylhexyl pentaethylene glycol ether sulfate;
2-ethylhexyl hexaethylene glycol ether sulfate;
2-ethylhexyl heptaethylene glycol ether sulfate;
2-ethylhexyl octaethylene glycol ether sulfate;
2-ethylhexyl nonaethylene glycol ether sulfate; and
2-ethylhexyl decaethylene glycol ether sulfate.

21. The adjuvant formulation according to claim 20;
wherein the 2-ethylhexyl (poly)glycol ether sulfate is 2-ethylhexyl tetraethylene glycol ether sulfate.

22. A 2-ethylhexyl (poly)glycol ether sulfate having 1 to 20 alkyleneoxy units in the ether moiety, each 2-ethylhexyl (poly)glycol ether sulfate having the formula:

$$R\text{—}O\text{—}(R^1O)_n\text{—}SO_3:$$

where:
R is 2-ethylhexyl;
$R^1$ is alkylene; and
n is 1 to 20;

wherein the 2-ethylhexyl (poly)glycol ether sulfate is selected from the group consisting of:
2-ethylhexyl ethylene glycol ether sulfate;
2-ethylhexyl diethylene glycol ether sulfate;
2-ethylhexyl triethylene glycol ether sulfate;
2-ethylhexyl tetraethylene glycol ether sulfate;
2-ethylhexyl hexaethylene glycol ether sulfate;
2-ethylhexyl heptaethylene glycol ether sulfate;
2-ethylhexyl octa ethylene glycol ether sulfate;
2-ethylhexyl nonaethylene glycol ether sulfate; and
2-ethylhexyl decaethylene glycol ether sulfate.

23. The 2-ethylhexyl (poly)glycol ether sulfate according to claim 22;
wherein the 2-ethylhexyl (poly)glycol ether sulfate is 2-ethylhexyl tetraethylene glycol ether sulfate.

24. The 2-ethylhexyl (poly)glycol ether sulfate according to claim 22;
wherein a counterion of the 2-ethylhexyl (poly)glycol ether sulfate is a sodium, potassium, or ammonium ion.

25. The 2-ethylhexyl (poly)glycol ether sulfate according to claim 24;
wherein the counterion is sodium.

26. A method for protecting a crop, comprising:
utilizing the adjuvant formulation according to claim 1.

27. A method for protecting a crop, comprising:
utilizing the 2-ethylhexyl (poly)glycol ether sulfate according to claim 22.

28. An adjuvant formulation comprising:
(c) from 0.1 to 99% by weight of one or more 2-ethylhexyl (poly)glycol ether sulfates having 1 to 20 alkyleneoxy units in the ether moiety, each 2-ethylhexyl (poly)glycol ether sulfate having the formula:

$$R\text{—}O\text{—}(R^1O)_n\text{—}SO_3:$$

where:
R is 2-ethylhexyl;
$R^1$ is alkylene; and
n is 1 to 20;
(d) from 0 to 30% by weight of one or more surfactants selected from the group consisting of anion-active, nonionic, cationic, and zwitterionic surfactants;
(e) from 0.1 to 95% by weight of water;
(f1) from 0 to 40% by weight of one or more polar organic solvents; and
(f) from 0 to 15% by weight of one or more other customary formulation auxiliaries;
wherein the 2-ethylhexyl (poly)glycol ether sulfate is selected from the group consisting of:
2-ethylhexyl ethylene glycol ether sulfate;
2-ethylhexyl diethylene glycol ether sulfate;
2-ethylhexyl triethylene glycol ether sulfate;
2-ethylhexyl tetraethylene glycol ether sulfate;
2-ethylhexyl pentaethylene glycol ether sulfate;
2-ethylhexyl hexaethylene glycol ether sulfate;
2-ethylhexyl heptaethylene glycol ether sulfate;
2-ethylhexyl octaethylene glycol ether sulfate;
2-ethylhexyl nonaethylene glycol ether sulfate; and
2-ethylhexyl decaethylene glycol ether sulfate.

29. The adjuvant formulation according to claim 28;
wherein:
component (c) is present in an amount of from 1 to 80% by weight;
component (d) is present in an amount of from 1 to 25% by weight;
component (e) is present in an amount of from 5 to 90% by weight; and component (f1) is present in an amount of from 0 to 30% by weight.

30. The adjuvant formulation according to claim 28; wherein component (c) is 2-ethylhexyl tetraethylene glycol ether sulphate sodium salt.

31. A method for protecting a crop, comprising:
utilizing the adjuvant formulation according to claim 28.

32. 2-ethylhexyl tetraethylene glycol ether sulphate sodium salt.

33. A method for protecting a crop, comprising:
utilizing the 2-ethylhexyl tetraethylene glycol ether sulphate sodium salt according to claim 32.

* * * * *